United States Patent
Stauffer

(10) Patent No.: US 9,169,168 B2
(45) Date of Patent: Oct. 27, 2015

(54) PROCESS FOR PRODUCING ETHYLENE BY CHLORINATION OF ETHANE AND DEHYDROCHLORINATION OF ETHYL CHLORIDE

(71) Applicant: John E. Stauffer, Greenwich, CT (US)

(72) Inventor: John E. Stauffer, Greenwich, CT (US)

(*) Notice: Subject to any disclaimer, the term of this patent is extended or adjusted under 35 U.S.C. 154(b) by 0 days.

(21) Appl. No.: 13/859,886

(22) Filed: Apr. 10, 2013

(65) Prior Publication Data

US 2014/0309468 A1   Oct. 16, 2014

(51) Int. Cl.
C07C 1/30 (2006.01)
C07C 2/86 (2006.01)
C07C 17/154 (2006.01)
C01B 7/03 (2006.01)

(52) U.S. Cl.
CPC . C07C 1/30 (2013.01); C01B 7/035 (2013.01); C07C 17/154 (2013.01); *C07C 2521/12* (2013.01); *C07C 2521/18* (2013.01); *C07C 2527/138* (2013.01)

(58) Field of Classification Search
CPC .......................................... C07C 1/30
USPC .................................. 585/314, 324, 641, 642
See application file for complete search history.

(56) References Cited

U.S. PATENT DOCUMENTS

| | | | | |
|---|---|---|---|---|
| 2,407,828 | A * | 9/1946 | Gorin | 570/190 |
| 2,725,411 | A * | 11/1955 | Ladd et al. | 570/189 |
| 3,173,962 | A * | 3/1965 | Carroll et al. | 570/243 |
| 3,325,554 | A * | 6/1967 | Addy | 502/174 |
| 3,352,935 | A * | 11/1967 | Kruse et al. | 585/632 |
| 3,609,103 | A * | 9/1971 | Gladrow et al. | 502/68 |
| 4,384,159 | A * | 5/1983 | Diesen | 585/642 |
| 4,849,562 | A * | 7/1989 | Buhs et al. | 570/241 |

OTHER PUBLICATIONS

Kenney, et al. ("The catalytic dehydrohalogenation of alkyl halides by fused zinc chloride and other molten chlorides" in Journal of Catalysis, 22(1) pp. 16-22, Jul. 1971).*

* cited by examiner

*Primary Examiner* — Aaron Pierpont
(74) *Attorney, Agent, or Firm* — Young Basile Hanlon & MacFarlane

(57) ABSTRACT

Ethylene is produced from ethane in three steps: first, ethane is oxychlorinated to produce ethyl chloride and water; second, ethyl chloride from the first step is cracked to produce ethylene and hydrogen chloride; and third, the hydrogen chloride from the second step is recycled to the front step.

1 Claim, 1 Drawing Sheet

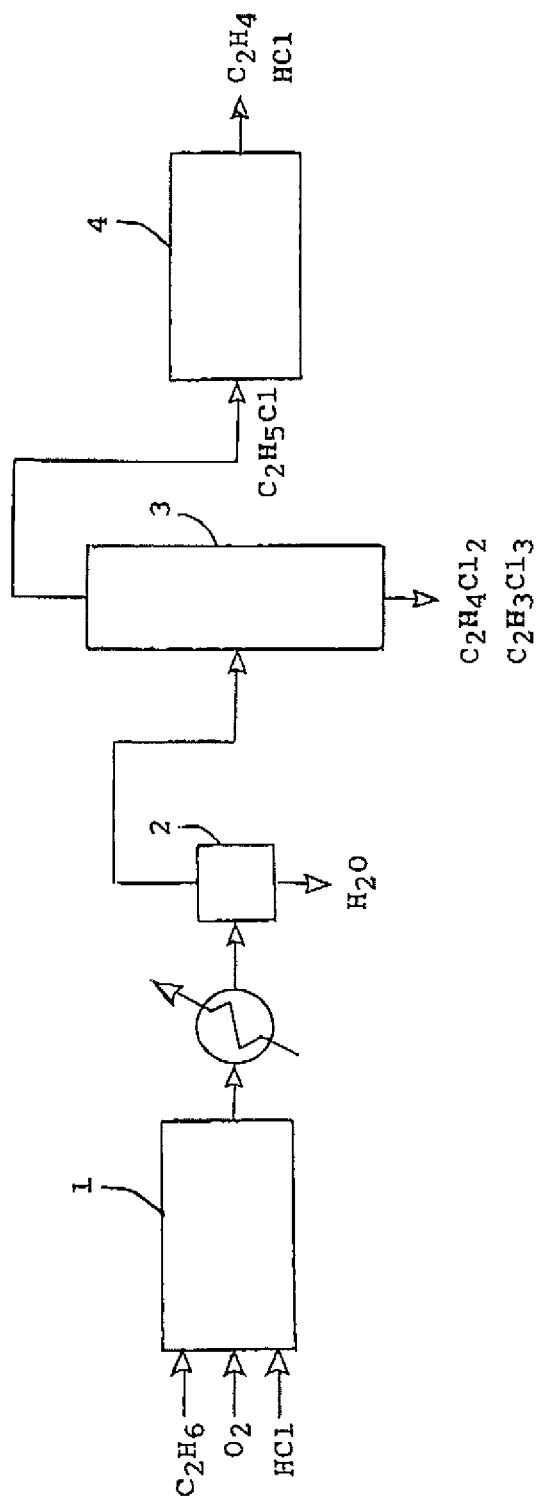

PROCESS FOR PRODUCING ETHYLENE BY CHLORINATION OF ETHANE AND DEHYDROCHLORINATION OF ETHYL CHLORIDE

FIELD OF THE INVENTION

The present invention relates to a process for manufacturing ethylene from ethane. The process comprises two chemical reactions. In the first reaction, ethane, oxygen and hydrogen chloride are passed over a catalyst to produce ethyl chloride and water. The second reaction converts ethyl chloride in the presence of a second catalyst to ethylene and hydrogen chloride.

BACKGROUND OF THE INVENTION

One of the principal routs to the production of ethylene involves cracking ethane at high temperatures. Purified ethane obtained from refinery gas streams or from natural gas is heated to temperatures of about 816° C. The thermal cracking, which takes place without a catalyst involves free radicals and a chain reaction.

The results of the thermal cracking depend on such variables as temperature, pressure and residence time, collectively referred to as cracking severity. Even under the best of conditions, numerous byproducts limit the production of ethylene. Thus, a representative yield of ethylene is about 80 percent.

Because of the formation of byproducts ranging from hydrogen and methane to butane and higher molecular weight hydrocarbons, extensive processing is needed to separate the ethylene product. This requirement is made more stringent because many of the uses of ethylene, for example, polyethylene production, demand high purity material.

For the above reasons, present know-how for producing ethylene from ethane has severe drawbacks. Capital investment is substantial and operating efficiencies are average.

SUMMARY OF THE INVENTION

It is an object of the present invention to offer alternative technology with favorable economics and robust features. This, as well as other objects and advantages of the present invention will become apparent from the following description and the figure that is included with this disclosure.

A process is provided for the synthesis of ethylene from ethane according to two chemical reactions operated in sequence. First, a stream comprising ethane, oxygen and hydrogen chloride is passed over an oxychlorination catalyst to produce ethyl chloride and water. The ethyl chloride obtained in the first reaction is next cracked over a second catalyst to form ethylene and hydrogen chloride. By optionally recycling the hydrogen chloride from the second reaction to the first reaction, there is no net consumption of this intermediate.

A key feature of the present invention is the oxychlorination catalyst. This catalyst contains the chlorides of copper, lead, and an alkali metal. Under operating conditions, this catalyst mix is molten.

A number of catalyst compositions are effective in cracking ethyl chloride. Among these catalysts are zinc chloride, activated carbon and silica alumina.

Operating conditions for the process are as follows. The oxychlorination of ethane is conducted at a temperature in the range of 350° to 400° C. An excess of ethane is advantageous in this reaction. The cracking of ethyl chloride takes place at a temperature in the range of 325° to 375° C. Both oxychlorination and cracking reactions are carried out at pressures in the range of 1 to 10 atmospheres.

Ethyl chloride produced as an intermediate in the present invention can be supplemented or replaced by ethyl chloride derived by the hydrochlorination of ethyl alcohol.

Other advantages, features and characteristics of the present invention, as well as methods of operation and functions of the related elements of the structure, and the combination of parts and economies of manufacture, will become more apparent upon consideration of the following detailed description and the appended claims with reference to the accompanying photographs, the latter being briefly described hereinafter.

BRIEF SUMMARY OF THE DRAWINGS

The description herein makes reference to the accompanying drawing wherein like reference numerals refer to like parts throughout the several views and wherein:

FIG. 1 is a block diagram showing the principal features of the process. Intermediate and product streams are indicated on the flow sheet.

DETAILED DESCRIPTION OF THE ILLUSTRATIVE EMBODIMENT

The advantages of the present invention are best understood through an appreciation of the relevant chemistry. The two chemical reactions that take place are illustrated by the following equations:

$$C_2H_6 + HCl + 0.5O_2 \rightarrow C_2H_5Cl + H_2O \qquad 1.$$

$$C_2H_5Cl \rightarrow C_2H_4 + HCl \qquad 2.$$

In these expressions, $C_2H_6$ represents ethane, HCl is hydrogen chloride, $O_2$ is oxygen, $C_2H_5Cl$ is ethyl chloride, $H_2O$ is water and $C_2H_4$ is ethylene.

When the above equations are combined, the overall process is represented as follows:

$$C_2H_6 + 0.5O_2 \rightarrow C_2H_4 + H_2O \qquad 3.$$

From equation 3, it is to be noted that there is no net consumption of chlorine or chlorine compounds.

Both reactions represented by equations 1 and 2 require catalysts to be effective. The reaction of equation 1, often known as oxychlorination, depends on the presence of a copper salt although other compounds such as those of iron are reported in the literature. Thus, copper chloride cycles back and forth from cupric chloride to cuprous chloride through the intermediate cupric oxychloride.

The second most important constituent of the chlorination catalyst is lead chloride. In essence this compound is a negative catalyst. Its presence inhibits the burning of ethane to carbon monoxide and carbon dioxide. In this regard, lead chloride is critical to the success of the present invention.

Finally, an alkali metal chloride is incorporated into the catalyst. Whether lithium, sodium, potassium or cesium chloride are used singly or together, an alkali metal chloride serves to depress the melting point of the catalyst mix. This phenomenon is important in increasing the catalyst activity.

The reaction shown by equation 2 also depends on a catalyst to take place. When ethyl chloride is heated to a high temperature in the range of 500° to 650° C. without a catalyst, hardly any ethylene product is obtained. At the upper end of this range, the principal reaction is the formation of carbon.

The effective catalysts for the reaction of equation 2 are numerous. However, three catalysts in particular are noteworthy. Activated charcoal shows some activity, but it is less effective than other catalysts. Zinc chloride provides outstanding conversions. The only drawback to zinc chloride is its volatility, so steps need to be taken to maintain its activity. Finally, silica alumina appears to meet all of the criteria of an effective catalyst: high activity, long life and good specificity.

Operating conditions for the process of the present invention are critical. The oxychlorination reaction shown by equation 1 requires a temperature in the range of 350° to 400° C. This reaction is exothermic so means must be provided to remove the heat of reaction. One approach is to use an excess of ethane in the feed. Not only will the surplus improve heat transfer, but it will also improve the yield of ethyl chloride by reducing the formation of higher chlorinated ethanes. When an excess of ethane is used, oxygen gas is the preferred oxidant instead of air.

In special situations where there is a surplus of ethyl alcohol such as that produced by the fermentation of biomass, ethyl chloride can be produced by reacting ethyl alcohol with hydrogen chloride. The classical preparation of ethyl chloride by this means uses a zinc chloride catalyst at a temperature in the range of 110° to 140° C.

The cracking operation illustrated by equation 2 functions best at a temperature in the range of 325° to 375° C. This reaction is endothermic so that heat must be supplied to the reactor. This requirement is facilitated by the use of a shell and tube reactor design, which also is recommended for the oxychlorination reaction.

The present invention is complicated by the formation of coproducts, but these compounds can be of some use. Ethane can be further chlorinated to produce ethylene dichloride and trichloroethane. Both of these compounds are valuable products. Ethylene dichloride can be cracked to produce vinyl chloride, and trichloroethane can also be cracked to give vinylidene chloride.

For a better appreciation of the present invention, FIG. 1 is helpful. This figure is a block diagram showing the principal pieces of equipment. Feed gases are introduced to oxychlorination reactor 1 and the effluent from the reactor is cooled in a heat exchanger before water is removed in phase separator 2. The chlorinated products pass to distillation column 3 where ethyl chloride is removed overhead from the higher chlorinated ethane coproducts. Next, the ethyl chloride is fed to cracking furnace 4 where ethylene and hydrogen chloride are formed. The exit gases are separated in an absorption apparatus (not shown) to produce the ethylene product and hydrogen chloride for recycling to the oxychlorination reactor. If an excess of ethane is used in the process, this reactant is also recycled.

EXAMPLE

The catalyst composition for the oxychlorination of ethane to ethyl chloride was 40 mol percent copper chloride, 30 mol percent potassium chloride, 10 mol percent sodium chloride, and 20 mol percent lead chloride. The reaction was run at 370° C. At steady state conditions, 81.4 percent of the ethane was unreacted, 14.0 percent converted to ethyl chloride, 0.6 percent converted to 1, 1 dichloroethane, 2.2 percent to ethylene dichloride, 1.4 percent to trichloroethane and 0.4 percent to tetrachloroethane. No carbon monoxide or carbon dioxide was detected. The ethyl chloride was cracked over a silica alumina catalyst at 350° C. to give a near quantitative yield of ethylene. The catalyst was 12.4 weight percent $Al_2O_3$ and 87.3 percent $SiO_2$ and had a surface area of 300 $m^2/g$.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:
1. A process for the manufacture of ethylene from ethane comprising the steps of:
  a) oxychlorinating ethane with hydrogen chloride and oxygen to give ethyl chloride and water at a temperature in the range of 350° to 400° C. in the presence of a catalyst;
  b) vapor phase cracking the ethyl chloride to give ethylene and hydrogen chloride at a temperature in the range of 325° to 375° C. over a catalyst consisting of silica alumina; and
  c) recycling hydrogen chloride produced in step b for use in step a.

* * * * *